United States Patent [19]

Katsura et al.

[11] Patent Number: 5,998,652
[45] Date of Patent: Dec. 7, 1999

[54] PROCESS FOR PREPARING 2-CYANOBIPHENYL COMPOUND

[75] Inventors: Tadashi Katsura; Hiroshi Shiratani; Kiyoshi Sugi; Nobushige Itaya, all of Osaka, Japan

[73] Assignee: Sumika Fine Chemicals Co., Ltd., Osaka, Japan

[21] Appl. No.: 09/009,823

[22] Filed: Jan. 20, 1998

[30] Foreign Application Priority Data

Jan. 21, 1997 [JP] Japan .................................. 9-023345
Feb. 4, 1997 [JP] Japan .................................. 9-036972

[51] Int. Cl.$^6$ ................................................. C07C 255/00
[52] U.S. Cl. ................................................. 558/411
[58] Field of Search ............................................ 558/411

[56] References Cited

U.S. PATENT DOCUMENTS

| | | | |
|---|---|---|---|
| 5,288,895 | 2/1994 | Bousset et al. | 558/378 |
| 5,380,910 | 1/1995 | Kageyama | 558/411 |

FOREIGN PATENT DOCUMENTS

| | | |
|---|---|---|
| 0566468 | 10/1993 | European Pat. Off. . |
| 69536 | 10/1993 | Japan . |
| 109143 | 4/1996 | Japan . |
| 231454 | 9/1996 | Japan . |

OTHER PUBLICATIONS

Masato, Patent Abstracts Of Japan, vol. 097, No. 001, Jan. 31, 1997 (JP 08231454A).

*Primary Examiner*—Johann Richter
*Assistant Examiner*—Joseph Murray
*Attorney, Agent, or Firm*—Birch, Stewart, Kolasch & Birch, LLP

[57] ABSTRACT

A process for preparing a 2-cyanobiphenyl compound represented by the formula (II):

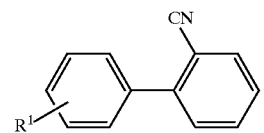

(II)

wherein $R^1$ is an alkyl group having 1 to 6 carbon atoms, an alkoxy group having 1 to 6 carbon atoms, or hydrogen atom, from a phenylmagnesium chloride compound represented by the formula (I):

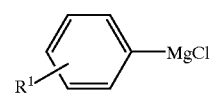

(I)

wherein $R^1$ is as defined above. According to the process, a 2-cyanobiphenyl compound represented by the formula (II) can be economically, simply, industrially and advantageously prepared.

12 Claims, No Drawings

PROCESS FOR PREPARING 2-CYANOBIPHENYL COMPOUND

BACKGROUND OF THE INVENTION

1. Field of the Invention

The present invention relates to a process for preparing a 2-cyanobiphenyl compound. More particularly, the present invention relates to a process for preparing a 2-cyanobiphenyl compound, which is useful as an intermediate of pharmaceuticals such as antihypertensives.

2. Discussion of the Related Art

Conventionally, there have been known processes for preparing 2-cyanobiphenyl compounds, including (A) a method of reacting a phenylmagnesium halide compound with a 2-halobenzonitrile in the presence of a manganese(II) halide (Japanese Patent Laid-Open No. Hei 6-9536); and (B) a method of reacting a phenylmagnesium halide compound with a 2-halobenzonitrile in the presence of a metal manganese and trimethylchlorosilane (Japanese Patent Laid-Open No. Hei 8-109143).

In the process (A), however, since the manganese(II) halide has hygroscopic property, there arises such a problem that much care is necessitated in handling.

In the process (B), since it is necessary to add an equimolar amount of a metal manganese to the 2-halobenzonitrile, the metal manganese has to be treated after terminating the reaction, thereby industrial wastes are generated. Therefore, this method is not industrially advantageous.

In addition, there have been known processes for preparing 4'-methyl-2-cyanobiphenyl, which is one of the 2-cyanobiphenyl compounds, including (C) a process for preparing 4'-methyl-2-cyanobiphenyl comprising treating a 4-methylphenylmagnesium halide and a 2-halobenzonitrile with a Ni catalyst in the presence of a zinc halide and an amine compound (Japanese Patent Laid-Open No. Hei 8-231454); and (D) a process for preparing 4'-methyl-2-cyanobiphenyl comprising reacting a phenylmagnesium halide with a zinc halide, and treating the resulting product with 4-bromobenzonitrile in the presence of a Ni catalyst (J. Org. Chem. 42. 1821, (1977)).

However, in the process (C), an expensive tertiary amine has to be used as an amine compound in order to give a reaction yield of at least 80%, and thereby there arise economical disadvantages.

In addition, in the process (D), an expensive bromide or iodide has to be used as a halide, which is a reaction substrate, and thereby there arise economical disadvantages as in the process (C).

In view of the problems in the prior art mentioned above, an object of the present invention is to provide a method for economically, advantageously, simply and industrially preparing a 2-cyanobiphenyl compound.

These and other objects of the present invention will be apparent from the following description.

SUMMARY OF THE INVENTION

In sum, the present invention pertains to the following:

(1) A process for preparing a 2-cyanobiphenyl compound represented by the formula (II):

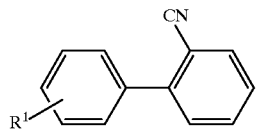

wherein $R^1$ is an alkyl group having 1 to 6 carbon atoms, an alkoxy group having 1 to 6 carbon atoms, or hydrogen atom, comprising the steps of:

adding manganese dioxide and trimethylchlorosilane to an ether-based organic solvent; and reacting a phenylmagnesium chloride compound represented by the formula (I):

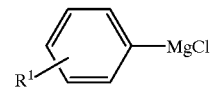

wherein $R^1$ is as defined above, with o-chlorobenzonitrile in the ether-based organic solvent; and (2) A process for preparing a 2-cyanobiphenyl compound represented by the formula (II):

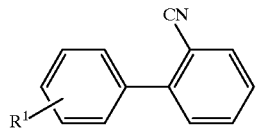

wherein $R^1$ is an alkyl group having 1 to 6 carbon atoms, an alkoxy group having 1 to 6 carbon atoms, or hydrogen atom, comprising the steps of:

reacting a phenylmagnesium chloride compound represented by the formula (I):

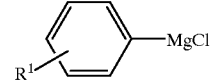

wherein $R^1$ is as defined above, with $ZnCl_2$; and reacting the resulting product with o-chlorobenzonitrile in the presence of both an aprotic polar solvent and an Ni catalyst.

DETAILED DESCRIPTION OF THE INVENTION

In the present invention, there are the following two embodiments for preparing a 2-cyanobiphenyl compound:

(1) A process for preparing a 2-cyanobiphenyl compound represented by the formula (II):

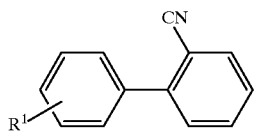

(II)

wherein R¹ is an alkyl group having 1 to 6 carbon atoms, an alkoxy group having 1 to 6 carbon atoms, or hydrogen atom, comprising the steps of:
  adding manganese dioxide and trimethylchlorosilane to an ether-based organic solvent; and
  reacting a phenylmagnesium chloride compound represented by the formula (I):

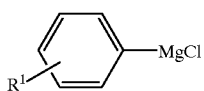

(I)

wherein R¹ is as defined above, with o-chlorobenzonitrile (hereinafter referred to as "Process I"); and (2) A process for preparing a 2-cyanobiphenyl compound represented by the above formula (II), comprising the steps of:
  reacting a phenylmagnesium chloride compound represented by the above formula (I), with $ZnCl_2$; and
  reacting the resulting product with o-chlorobenzonitrile in the presence of both an aprotic polar solvent and an Ni catalyst (hereinafter referred to as "Process II").

In both Process I and Process II mentioned above, the phenylmagnesium chloride compound represented by the formula (I) is used as a starting material.

R¹ in the above formula (I) is an alkyl group having 1 to 6 carbon atoms, an alkoxy group having 1 to 6 carbon atoms, or hydrogen atom.

The alkyl groups having 1 to 6 carbon atoms mentioned above include, for instance, linear or branched alkyl groups having 1 to 6 carbon atoms. Concrete examples of the alkyl groups having 1 to 6 carbon atoms include methyl group, ethyl group, n-propyl group, isopropyl group, n-butyl group, isobutyl group, sec-butyl group, tert-butyl group, pentyl group, hexyl group, and the like. When R¹ is methyl group, 4'-methyl-2-cyanobiphenyl, which is useful as an intermediate for pharmaceuticals such as antihypertensives, can be prepared.

Concrete examples of the alkoxy groups having 1 to 6 carbon atoms include, for instance, methoxy group, ethoxy group, n-propoxy group, isopropoxy group, n-butoxy group, isobutoxy group, sec-butoxy group, tert-butoxy group, pentyloxy group, hexyloxy group, and the like.

Concrete examples of the phenylmagnesium chloride compound represented by the formula (I) include, for instance, phenylmagnesium chloride, o-methylphenylmagnesium chloride, m-methylphenylmagnesium chloride, p-methylphenylmagnesium chloride, o-ethylphenylmagnesium chloride, m-ethylphenylmagnesium chloride, p-ethylphenylmagnesium chloride, o-n-propylphenylmagnesium chloride, m-n-propylphenylmagnesium chloride, p-n-propylphenylmagnesium chloride, o-isopropylphenylmagnesium chloride, m-isopropylphenylmagnesium chloride, p-isopropylphenylmagnesium chloride, o-n-butylphenylagnesium chloride, m-n-butylphenylmagnesium chloride, p-n-butylphenylmagnesium chloride, o-isobutylphenylmagnesium chloride, m-isobutylphenylmagnesiun chloride, p-isobutylphenylmagnesium chloride, o-sec-butylphenylmagnesium chloride, m-sec-butylphenylmagnesium chloride, p-sec-butylphenylmagnesium chloride, o-tert-butylphenylmagnesium chloride, m-tert-butylphenylmagnesium chloride, p-tert-butylphenylmagnesium chloride, o-pentylphenylmagnesium chloride, m-pentylphenylmagnesium chloride, p-pentylphenylmagnesium chloride, o-hexylphenylmagnesium chloride, m-hexylphenylmagnesium chloride, p-hexylphenylmagnesium chloride, o-methoxyphenylmagnesium chloride, m-methoxyphenylmagnesium chloride, p-methoxyphenylmagnesium chloride, o-ethoxyphenylmagnesium chloride, m-ethoxyphenylmagnesium chloride, p-ethoxyphenylmagnesium chloride, o-n-propoxyphenylmagnesium chloride, m-n-propoxyphenylmagnesium chloride, p-n-propoxyphenylmagnesium chloride, o-isopropoxyphenylmagnesium chloride, m-isopropoxyphenylmagnesium chloride, p-isopropoxyphenylmagnesium chloride, o-n-butoxyphenylmagnesium chloride, m-n-butoxyphenylmagnesium chloride, p-n-butoxyphenylmagnesium chloride, o-isobutoxyphenylmagnesium chloride, m-isobutoxyphenylmagnesium chloride, p-isobutoxyphenylmagnesium chloride, o-sec-butoxyphenylmagnesium chloride, m-sec-butoxyphenylmagnesium chloride, p-sec-butoxyphenylmagnesium chloride, o-tert-butoxyphenylmagnesium chloride, m-tert-butoxyphenylmagnesium chloride, p-tert-butoxyphenylmagnesium chloride, o-pentyloxyphenylmagnesium chloride, m-pentyloxyphenylmagnesium chloride, p-pentyloxyphenylmagnesium chloride, o-hexyloxyphenylmagnesium chloride, m-hexyloxyphenylmagnesium chloride, p-hexylphenylmagnesium chloride, and the like.

Among the above phenylmagnesium chloride compounds, when the p-methylphenylmagnesium chloride is used, 4'-methyl-2-cyanobiphenyl, which is useful as an intermediate for pharmaceuticals such as antihypertensives, can be prepared. Therefore, the p-methylphenylmagnesium chloride can be particularly advantageously used.

In both of Process I and Process II, the phenylmagnesium chloride represented by the formula (I) is used as a starting material, to give a 2-cyanobiphenyl compound represented by the formula (II).

First, Process I will be described in detail below.

In Process I, manganese dioxide and trimethylchlorosilane are firstly added to an ether-based organic solvent.

Here, the ether-based organic solvent may be a solvent of ether alone or a mixed solvent of an ether and other organic solvents. In the present invention, it is desired that the ether-based organic solvent is substantially composed of the ether. The other organic solvents may be added in an amount so as not to impair the object of the present invention.

Concrete examples of the ethers include, for instance, tetrahydrofuran, diisopropyl ether, tert-butyl methyl ether, and the like. The ether may be used alone or in combination. A preference is given to tetrahydrofuran.

The other organic solvents may be any organic solvents which are unreactive with the phenylmagnesium chloride compound. The other organic solvents include those which are unreactive with Grignard reagents, and concrete examples thereof include, for instance, aromatic hydrocarbons, such as toluene and xylene.

It is desired that the amount of the ether-based organic solvent is at least 100 parts by weight, preferably from 200 to 2500 parts by weight, based on 100 parts by weight of o-chlorobenzonitrile described below.

One of the features of Process I is in the use of manganese dioxide. The manganese dioxide has advantageous merits in that the manganese dioxide has small hygroscopic property and thus can be easily handled.

The amount of the manganese dioxide may be a catalytic amount to o-chlorobenzonitrile described below. In other words, from the aspects of economical advantages and reactivity, it is desired that the amount of the manganese dioxide is from 0.01 to 0.3 mol, preferably from 0.02 to 0.2 mol, per mol of o-chlorobenzonitrile.

It is desired that the amount of the trimethylchlorosilane is from 0.01 to 1 mol, preferably from 0.02 to 0.5 mol, per mol of o-chlorobenzonitrile from the aspects of economical advantages and reactivity.

After manganese dioxide and trimethylchlorosilane are added to the ether-based organic solvent, the phenylmagnesium chloride compound represented by the formula (I) is reacted with o-chlorobenzonitrile in the ether-based organic solvent.

It is desired that the amount of the phenylmagnesium chloride compound is from 1 to 3 mol, preferably from 1 to 2 mol, per mol of o-chlorobenzonitrile from the aspects of economical advantages and reactivity.

It is desired that the lower limit of the reaction temperature during the reaction of the phenylmagnesium chloride compound with o-chlorobenzonitrile is at least −40° C., preferably at least −20° C., and the upper limit of the reaction temperature is at most 50° C., preferably at most 30° C., more preferably at most 10° C.

The atmosphere during the reaction is not particularly limited, and it is desired that the atmosphere is an inert gas atmosphere, such as nitrogen gas.

The reaction time cannot be absolutely determined because the reaction time can differ depending upon the reaction temperature, and the like. The reaction time is usually from 2 to 10 hours or so.

According to the above method, the 2-cyanobiphenyl compound represented by the formula (II), which is the desired compound in the present invention, can be prepared.

Incidentally, after the reaction is terminated, the 2-cyanobiphenyl compound can be isolated by conventional procedures of filtration, washing, extraction, concentration, distillation, and crystallization.

Furthermore, Process II will be described in detail below.

In Process II, since the phenylmagnesium chloride compound represented by the formula (I) is reacted with $ZnCl_2$, and the resulting product is then reacted with o-chlorobenzonitrile in the presence of both an aprotic polar solvent and an Ni catalyst, excellent effects that the 2-cyanobiphenyl compound represented by the formula (II) can be unexpectedly obtained in a very high efficiency.

In Process II, the phenylmagnesium chloride compound represented by the formula (I) is firstly reacted with $ZnCl_2$.

When the reaction of the phenylmagnesium chloride compound with $ZnCl_2$ is carried out, an ether-based organic solvent can be used as a solvent.

Examples of the ether-based organic solvents can be the same as those usable in Process I described above.

The amount of the ether-based organic solvent is not particularly limited, and it is desired that the amount of the ether-based organic solvent is from 100 to 1000 parts by weight or so, based on 100 parts by weight of the phenylmagnesium chloride compound.

Incidentally, the phenylmagnesium chloride compound may be previously dissolved in the ether-based organic solvent.

It is desired that the amount of $ZnCl_2$ is from 0.9 to 1.2 mol or so per mol of the phenylmagnesium chloride compound from the aspects of economical advantages and reactivity.

Incidentally, it is desired that the atmosphere during the reaction of the phenylmagnesium chloride compound with $ZnCl_2$ is an inert gas, such as nitrogen gas, or argon gas. In addition, the pressure of the atmosphere is not particularly limited, and it is desired that the pressure is usually an atmospheric pressure.

In addition, it is desired that the reaction temperature is from 0° to 70° C. or so.

The reaction time cannot be absolutely determined because the reaction time can differ depending upon the reaction temperature, and the like. The reaction time is usually from 0.5 to 10 hours or so.

In Process II, after the reaction is terminated, the reaction mixture can be directly used to react with o-chlorobenzonitrile without taking out the resulting reaction product from the reaction mixture.

One of the large features of Process II resides in the use of an aprotic polar solvent during the reaction of the above reaction product with o-chlorobenzonitrile.

The aprotic polar solvent, which is used in Process II, is an extremely inexpensive, easily available compound. Moreover, when the aprotic polar solvent is used, the 2-cyanobiphenyl compound, which is a desired compound in the present invention, can be advantageously obtained in a high yield.

Concrete examples of the aprotic polar solvents include, for instance, dimethylformamide, dimethylacetamide, N-methyl-2-pyrrolidone, dimethylsulfoxide, and the like. Those aprotic polar solvents can be used alone or in admixture thereof.

From the aspects of high yields and economical advantages, it is desired that the amount of the aprotic polar solvent is from 0.1 to 3 mol, preferably from 0.5 to 2 mol, per mol of o-chlorobenzonitrile.

Another feature of Process II resides in the use of an Ni catalyst.

Concrete examples of the Ni catalysts include, for instance, nickel(II) dichlorobis(triphenylphosphine), nickel (II) dibromobis(triphenylphosphine), and the like.

It is desired that the amount of the Ni catalyst is from 0.01 to 0.3 mol, preferably from 0.02 to 0.2 mol, per mol of o-chlorobenzonitrile.

In this case, the amount of the ether-based organic solvent is not particularly limited, and it is desired that the amount of the ether-based organic solvent is at least 100 parts by weight, preferably from 200 to 2500 parts by weight, based on 100 parts by weight of o-chlorobenzonitrile.

In addition to o-chlorobenzonitrile, the aprotic polar solvent and the Ni catalyst can also be dissolved in the ether-based organic solvent prior to the reaction.

The reaction of the resulting reaction product with o-chlorobenzonitrile can be carried out, for instance, by a process comprising, dissolving o-chlorobenzonitrile, an aprotic polar solvent and an Ni catalyst in an ether-based organic solvent to give a mixture, and adding dropwise the reaction mixture containing the above reaction product to the resulting mixture.

It is desired that the amount of the phenylmagnesium chloride compound, which is a starting material of the reaction product, is from 1 to 3 mol or so, preferably from 1 to 2 mol or so, per mol of o-chlorobenzonitrile.

Incidentally, it is desired that the atmosphere during the reaction is an inert gas, such as nitrogen gas, or argon gas. In addition, the pressure of the atmosphere is not particularly limited, and it is desired that the pressure is usually an atmospheric pressure.

It is desired that the lower limit of the reaction temperature during the reaction of the phenylmagnesium chloride compound with o-chlorobenzonitrile is at least −5° C., preferably at least 20° C., more preferably at least 40° C., and the upper limit of the reaction temperature is at most 80° C., preferably at most 60° C.

The reaction time cannot be absolutely determined because the reaction time can differ depending upon the reaction temperature, and the like. The reaction time is usually from 0.5 to 10 hours or so. Thus, the 2-cyanobiphenyl compound represented by the formula (II), which is a desired compound in the present invention, can be obtained. In order to increase the purity of the 2-cyanobiphenyl compound, the organic layer can be separated from the reaction mixture using hydrochloric acid and the like and washed with brine. Thereafter, the resulting organic layer can be isolated by distillation to purify. Also, the 2-cyanobiphenyl compound purified by distillation can be further treated with activated carbon, silica gel, or alumina, to further increase its purity.

The 2-cyanobiphenyl compound prepared by Process I and Process II can be used in the preparation of intermediates for pharmaceuticals such as antihypertensives.

EXAMPLES

The present invention will be more specifically described by the following examples, without intending to restrict the scope or spirit of the present invention thereto.

Example 1

A one-liter flask was charged with 2.09 g (0.024 mol) of manganese dioxide, 10.4 g (0.096 mol) of trimethylchlorosilane, and 206 g of tetrahydrofuran, and the resulting mixture was stirred for three hours at a temperature of from 40° to 45° C. Thereafter, 41.3 g (0.3 mol) of o-chlorobenzonitrile was added to the above mixture, and the resulting mixture was cooled to a temperature of from 0° to 5° C.

Subsequently, 400 g of a tetrahydrofuran solution of p-methylphenylmagnesium chloride (concentration of p-methylphenylmagnesium chloride: 19.8% by weight; and content of p-methylphenylmagnesium chloride: 0.52 mol) was added dropwise to the flask at a temperature of 0° to 5° C. over a period of six hours, and the mixture was kept at that temperature for one hour to be reacted.

After the reaction was terminated, 100 ml of a 12% by weight-aqueous hydrochloric acid was poured into the flask, and the mixture was allowed to stand for 30 minutes. Thereafter, the organic layer was separated and washed with 100 ml of a 15% by weight brine.

Next, the solvent contained in the resulting organic layer was distilled off, to give 73.1 g (0.249 mol) of crude 4'-methyl-2-cyanobiphenyl.

The resulting crude 4'-methyl-2-cyanobiphenyl was subjected to high-performance liquid chromatography analysis (HPLC analysis). As a result, it was found that the purity of the 4'-methyl-2-cyanobiphenyl was 65.9% by weight, and the yield was 83.1% by mol.

Subsequently, 73.1 g of the resulting crude 4'-methyl-2-cyanobiphenyl was purified by distillation. As a result, 4'-methyl-2-cyanobiphenyl having a purity of 98.4% by weight was obtained.

Further, 40.2 g of the resulting 4'-methyl-2-cyanobiphenyl purified by distillation was recrystallized from 200 g of n-heptane, to give 36.2 g of 4'-methyl-2-cyanobiphenyl having a purity of 99.2% by weight.

The obtained compound was identified as 4'-methyl-2-cyanobiphenyl by the following properties:

(1) Melting point: 52.1°–53.2° C.

(2) $^1$H-NMR (DMSO-$d_6$) δ (ppm): 7.95 (d, 1H, J=8 Hz), 7.78 (t, 1H, J=8Hz), 7.69–7.32 (m, 6H), 2.39 (s, 3H).

Example 2

A one-liter flask was charged with 65.4 g (0.48 mol) of $ZnCl_2$ and 325 g of tetrahydrofuran. Thereafter, 360 g of a tetrahydrofuran solution of p-methylphenylmagnesium chloride (concentration of the p-methylphenylmagnesium chloride: 20.1% by weight; and content of the p-methylphenylmagnesium chloride: 0.48 mol) was added dropwise to the flask at a temperature of 30° to 40° C. over a period of 30 minutes, and the mixture was kept at that temperature for one hour, to give slurry of a p-methylphenylzinc compound in tetrahydrofuran.

On the other hand, separately, a two-liter flask was charged with 7.85 g (0.012 mol) of nickel(II) dichlorobis (triphenylphosphine) as an Ni catalyst, 41.8 g (0.48 mol) of dimethylacetamide as an aprotic polar solvent, 206 g of tetrahydrofuran as an ether-based solvent, and 41.3 g (0.3 mol) of o-chlorobenzonitrile, and the resulting mixture was heated to a temperature of from 45° to 50° C.

Next, the slurry of the p-methylphenylzinc compound in tetrahydrofuran prepared above was added dropwise to the two-liter flask at a temperature of 45° to 50° C. over a period of three hours, and the mixture was kept at that temperature to be reacted.

After the reaction was terminated, 400 ml of a 3% by weight-aqueous hydrochloric acid was poured into the flask, and the mixture was allowed to stand for 30 minutes. Thereafter, the organic layer was separated and washed with 400 ml of a 15% by weight brine.

Next, the solvent contained in the resulting organic layer was distilled off, to give 70.8 g of crude 4'-methyl-2-cyanobiphenyl.

The resulting crude 4'-methyl-2-cyanobiphenyl was subjected to HPLC analysis. As a result, it was found that the purity of the 4'-methyl-2-cyanobiphenyl was 69.5% by weight, and reaction yield was 84.9% by mol.

Subsequently, 70.8 g of the resulting crude 4'-methyl-2-cyanobiphenyl was purified by distillation. As a result, 41.5 g of 4'-methyl-2-cyanobiphenyl having purity of 97.5% by weight was obtained.

41.5 g of the 4'-methyl-2-cyanobiphenyl purified by distillation was dissolved in 200 g of n-heptane. Two grams of alumina was added to the above mixture, and the resulting mixture was heated at 50° to 60° C. for 30 minutes with stirring.

Thereafter, the alumina was filtered off, and the crystals were then precipitated by cooling the mixture. The crystals were filtrated, and the obtained crystals were washed with n-heptane, to give 36.0 g of 4'-methyl-2-cyanobiphenyl having a purity of 99.8% by weight. The resulting product had a melting point of 52.9° to 53.5° C.

Example 3

Similar procedures as in Example 1 were carried out except for adding dropwise 280 g of a tetrahydrofuran solution of p-methylphenylmagnesium chloride (concentration of p-methylphenylmagnesium chloride: 20.2% by weight; and content of the p-methylphenylmagnesium chloride: 0.375 mol) at a temperature of −35° to −30° C. over a period of five hours to obtain a separated organic layer.

The solvent of the resulting organic layer was distilled off, to give 59.4 g (0.257 mol) of crude 4'-methyl-2-cyanobiphenyl.

The purity of the resulting crude product determined by HPLC was 83.6% by weight, and the yield was 85.8% by mol.

Subsequently, 59.4 g of the resulting crude 4'-methyl-2-cyanobiphenyl was purified by distillation. As a result, 46.0 g of 4'-methyl-2-cyanobiphenyl having purity of 98.0% by weight was obtained.

46.0 g of the 4'-methyl-2-cyanobiphenyl purified by distillation was dissolved in 220 g of n-heptane. 2.2 grams of alumina was added to the above mixture, and the resulting mixture was heated at 50° to 60° C. for 30 minutes with stirring.

Thereafter, the alumina was filtered off, and the crystals were then precipitated by cooling the mixture. The crystals were filtrated, and the obtained crystals were washed with n-heptane, to give 40.0 g of 4'-methyl-2-cyanobiphenyl having a purity of 99.3% by weight. The resulting product had a melting point of 52.9° to 53.5° C.

Example 4

A two-liter flask was charged with 4.73 g (0.0544 mol) of manganese dioxide, 23.64 g (0.2176 mol) of trimethylchlorosilane, and 956 g of tetrahydrofuran, and the resulting mixture was stirred for three hours at a temperature of from 40° to 45° C. Thereafter, 18.72 g (0.136 mol) of o-chlorobenzonitrile was added to the above mixture, and the resulting mixture was cooled to −30° C.

Subsequently, 428 g of a tetrahydrofuran solution of p-methylphenylmagnesium chloride (concentration of p-methylphenylmagnesium chloride: 30.0% by weight; and content of p-methylphenylmagnesium chloride: 0.85 mol), and a mixed solution of 74.88 g (0.544 mol) of o-chlorobenzonitrile and 29.21 g of tetrahydrofuran were simultaneously added dropwise to the flask at a temperature of −35° to −30° C. over a period of 6.5 hours, and the mixture was kept at that temperature for one hour to be reacted.

After the reaction was terminated, 200 ml of a 12% by weight-aqueous hydrochloric acid was poured into the flask, and the mixture was allowed to stand for 30 minutes. Thereafter, the organic layer was separated and washed with 200 ml of a 15% by weight brine.

Next, the solvent contained in the resulting organic layer was distilled off, to give 132.6 g (0.566 mol) of crude 4'-methyl-2-cyanobiphenyl.

Also, the resulting crude 4'-methyl-2-cyanobiphenyl was subjected to high-performance liquid chromatography analysis (HPLC analysis). As a result, it was found that the purity of the 4'-methyl-2-cyanobiphenyl was 82.5% by weight, and reaction yield was 83.3% by mol.

As is clear from the above results, the 2-cyanobiphenyl compound can be prepared in a simple manner in high yields according to the processes described in Examples 1 to 4.

According to the process of the present invention, the 2-cyanobiphenyl compound can be economically, simply, industrially and advantageously prepared.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing a 2-cyanobiphenyl compound represented by the formula (II):

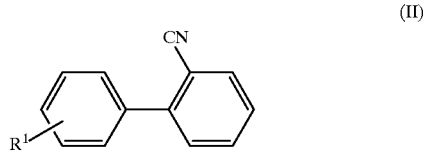

(II)

wherein $R^1$ is an alkyl group having 1 to 6 carbon atoms, an alkoxy group having 1 to 6 carbon atoms, or hydrogen atom, comprising the steps of:

adding manganese dioxide and trimethylchlorosilane to an ether-based organic solvent; and reacting a phenylmagnesium chloride compound represented by the formula (I):

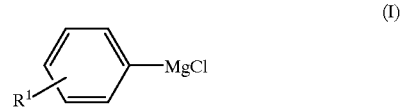

(I)

wherein $R^1$ is as defined above, with o-chlorobenzonitrile in the ether-based organic solvent.

2. The process for preparing a 2-cyanobiphenyl compound of claim 1, wherein $R^1$ is methyl group.

3. The process for preparing a 2-cyanobiphenyl compound of claim 1, wherein said ether-based organic solvent is tetrahydrofuran.

4. The process for preparing a 2-cyanobiphenyl compound of claim 1, wherein the amount of manganese dioxide is from 0.01 to 0.3 mol per mol of o-chlorobenzonitrile.

5. The process for preparing a 2-cyanobiphenyl compound of claim 1, wherein the amount of trimethylchlorosilane is from 0.01 to 1 mol per mol of o-chlorobenzonitrile.

6. The process for preparing a 2-cyanobiphenyl compound of claim 1, wherein the amount of the phenylmagnesium chloride compound is from 1 to 3 mol per mol of o-chlorobenzonitrile.

7. A process for preparing a 2-cyanobiphenyl compound represented by the formula (II):

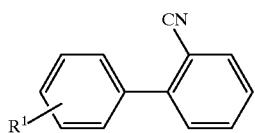

wherein R¹ is an alkyl group having 1 to 6 carbon atoms, an alkoxy group having 1 to 6 carbon atoms, or hydrogen atom, comprising the steps of:

reacting a phenylmagnesium chloride compound represented by the formula (I):

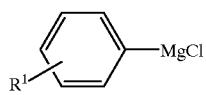

wherein R¹ is as defined above, with $ZnCl_2$; and reacting the resulting product with o-chlorobenzonitrile in the presence of both an aprotic polar solvent and an Ni catalyst.

8. The process for preparing a 2-cyanobiphenyl compound of claim 7, wherein R¹ is methyl group.

9. The process for preparing a 2-cyanobiphenyl compound of claim 7, wherein the amount of the phenylmagnesium chloride compound is from 1 to 3 mol per mol of o-chlorobenzonitrile.

10. The process for preparing a 2-cyanobiphenyl compound of claim 7, wherein the amount of $ZnCl_2$ is from 0.9 to 1.2 mol per mol of the phenylmagnesium chloride compound.

11. The process for preparing a 2-cyanobiphenyl compound of claim 7, wherein said Ni catalyst is nickel(II) dichlorobis(triphenylphosphine) or nickel(II) dibromobis(triphenylphosphine).

12. The process for preparing a 2-cyanobiphenyl compound of claim 7, wherein said aprotic polar solvent is dimethylformamide, dimethylacetamide, N-methyl-2-pyrrolidone or dimethylsulfoxide.

* * * * *